US007678387B2

(12) United States Patent
Cherukuri

(10) Patent No.: US 7,678,387 B2
(45) Date of Patent: Mar. 16, 2010

(54) DRUG DELIVERY SYSTEMS

(75) Inventor: S. Rao Cherukuri, Frederick, MD (US)

(73) Assignee: Capricorn Pharma, Inc., Frederick, MD (US)

( * ) Notice: Subject to any disclaimer, the term of this patent is extended or adjusted under 35 U.S.C. 154(b) by 0 days.

(21) Appl. No.: 09/982,093

(22) Filed: Oct. 19, 2001

(65) Prior Publication Data
US 2002/0044960 A1 Apr. 18, 2002

Related U.S. Application Data

(63) Continuation-in-part of application No. 09/587,971, filed on Jun. 6, 2000, now Pat. No. 6,555,145.

(60) Provisional application No. 60/308,568, filed on Jul. 31, 2001.

(51) Int. Cl.
A61K 9/20 (2006.01)
A61K 9/14 (2006.01)
(52) U.S. Cl. ...................... 424/464; 424/484
(58) Field of Classification Search ............... 424/451, 424/452, 461, 463, 464, 457, 473, 484; 514/394
See application file for complete search history.

(56) References Cited

U.S. PATENT DOCUMENTS

| 4,053,632 A * | 10/1977 | Carnmalm et al ........... 514/756 |
| 4,568,560 A | 2/1986 | Schobel |
| 4,740,376 A | 4/1988 | Yang |
| 4,975,270 A | 12/1990 | Kehoe |
| 4,981,698 A | 1/1991 | Cherukuri et al. |
| 5,004,595 A | 4/1991 | Cherukuri et al. |
| 5,266,335 A | 11/1993 | Cherukuri et al. |
| 5,283,065 A * | 2/1994 | Doyon et al. ................. 424/467 |
| 5,296,233 A * | 3/1994 | Batista et al. ................ 424/463 |
| 5,431,922 A * | 7/1995 | Nicklasson .................. 424/490 |
| 5,541,210 A * | 7/1996 | Cupps et al. ................. 514/394 |
| 5,762,961 A * | 6/1998 | Roser et al. .................. 424/464 |
| 5,866,585 A * | 2/1999 | Fogel .......................... 514/289 |
| 5,869,097 A * | 2/1999 | Wong et al. .................. 424/473 |
| 5,919,780 A * | 7/1999 | Bolton et al. ................ 514/220 |
| 6,197,828 B1 * | 3/2001 | Jerussi et al. ................ 514/648 |
| 6,245,350 B1 * | 6/2001 | Amey et al. .................. 424/456 |
| 6,274,171 B1 * | 8/2001 | Sherman et al. ............. 424/461 |
| 6,294,530 B1 * | 9/2001 | Zhang et al. ........... 514/212.05 |
| 6,306,436 B1 * | 10/2001 | Chungi et al ................ 424/464 |
| 6,562,375 B1 * | 5/2003 | Sako et al. ................... 424/486 |
| 2002/0015731 A1 * | 2/2002 | Appel et al. ................. 424/473 |

FOREIGN PATENT DOCUMENTS

EP 0 273 001 6/1988

OTHER PUBLICATIONS

Munday et al. "In vitro-in vivo correlation stidies on a novel controlled release theophylline delivery and on Theo-Dur tablets," in Internationa Journal of Pharmaceutics, 118 (1995), 251-255.*
van Sweden B. "Rebound insomnia in neuroleptic drug withdrawal neurophysiologic characteristics" in Pharmacopsychiatry, May 1987; 20 (3): abstract.*

* cited by examiner

Primary Examiner—Blessing M Fubara
(74) Attorney, Agent, or Firm—Hunton & Williams LLP

(57) ABSTRACT

A novel encapsulated product is provided and includes: at least one pharmaceutical; at least one compressible material; and at least one tableting material; wherein the encapsulated product is in the form of a caplet having a diameter of from about 1 millimeter to about 7 millimeters and a length from about 1 millimeter to about 7 millimeters. A method for preparing the encapsulated product is also provided.

18 Claims, No Drawings

DRUG DELIVERY SYSTEMS

This application is a nonprovisional Continuation-In-Part Application of provisional U.S. Patent Application No. 60/308,568 filed Jul. 31, 2001 and is a Continuation-In-Part Application of U.S. patent application Ser. No. 09/587,971 filed Jun. 6, 2000, now U.S. Pat. No. 6,555,145 the entire contents of which are hereby incorporated by reference in their entirety.

BACKGROUND OF THE INVENTION

1. Field of the Invention

The present invention relates to an encapsulation process, and in particular, an alternate encapsulation process for concentrating pharmaceuticals using compression.

2. Description of the Prior Art

Various types of chewable articles are known in commerce. These articles include food items such as food items, confectionery items and chewing gum. The chewable articles often include various types of active agents or ingredients within the chewable articles. Examples of such active ingredients include flavors, sweeteners, colors, pharmaceuticals, vitamins, minerals, and other effervescent agents.

It has been known in the art of food stuff, confectionery and chewing gum preparation to provide protection to the active ingredients by the use of protection systems, including providing a protective coating around the active ingredient or encapsulating the active ingredient. Such protective systems have been employed for various reasons, such as for protection of the active ingredient, both while on the shelf and during use, and for prolonged release in the oral cavity.

It is known in the art to protect active ingredients by encapsulating the active ingredient prior to introducing the ingredient into a final product. Some of the major classifications of encapsulation technology include liquid suspending media (water-in-oil emulsions and oil-in-water emulsions), interfacial and in situ polymerization, solvent evaporation from emulsions, desolvation, complex coacervation, polymer and polymer incompatibility, gelation, and pressure extrusion. One of skill in the art will be familiar with each of these classifications.

Schobel, U.S. Pat. No. 4,568,560, discloses encapsulated fragrances and flavors for use in denture cleanser compositions. Schobel discloses encapsulating a solid particulate flavoring agent or fragrance with a film of an acrylic polymer and ethylcellulose. The encapsulation is accomplished utilizing a fluidized bed of the flavoring agent or fragrance.

Yang, U.S. Pat. No. 4,740,376, discloses encapsulating an active ingredient in a solvent free encapsulation composition which includes a blend of a high molecular weight polyvinyl acetate and a hydrophilic plasticizer. The active ingredient is protected from deterioration due to moisture and is provided with controlled release for use in a product to be ingested by a mammal.

Cherukuri et al., U.S. Pat. No. 4,981,698, discloses a delivery system for sweeteners that comprises a first high intensity sweetener encapsulated in a first core coating, and a second outer hydrophilic coating containing up to the solubility limit of the second coating of a second sweetener. The delivery system offers enhanced up front sweetness intensity in combination with prolonged sweetness duration, and improved protection and stability of the sweetener.

Cherukuri et al., U.S. Pat. No. 5,004,595, discloses a free-flowing particulate delivery system for providing enhanced flavor and sweetness to comestible products. The delivery system includes an encapsulating matrix that protects flavor in a core.

Cherukuri et al., U.S. Pat. No. 5,266,335, discloses microencapsulated flavoring agents and methods for preparing the same. The microencapsule comprises a flavoring agent and a resin in the core, and a coating layer over the core. The core is encapsulated by emulsion of a flavoring agent and a resin with a coating layer prepared by complex coacervation of a mixture of two or more colloidal materials.

Kehoe, U.S. Pat. No. 4,975,270, discloses elastomer encased active ingredients. The active ingredients are physically encased in non-porous, chewable particles of elastomer. The particles are then incorporated into articles of commerce.

There are a number of disadvantages when using the traditional encapsulation processes to encapsulate active ingredients. The disadvantages include the need for heat and moisture in order to properly form the encapsulated final product. Also, most encapsulation methods are complex and consume large amounts of time in order to obtain the final encapsulated product. Further, current encapsulated ingredients vary in size from nanometers to about 400 microns, and the active ingredients are not uniformly distributed throughout the encapsulated product.

Therefore, there remains a need for an alternate encapsulation method for providing a product with high levels of active ingredients and in which water is not needed during the encapsulation process, nor is heat an essential feature of the encapsulation process. There also remains a need for an alternate encapsulation method which produces capsules with uniform active ingredient content throughout the product, and that can withstand mechanical pressure both in the processing of the capsule and in the chewing of the product in the mouth so that the active ingredients are released in the stomach of the consumer.

BRIEF SUMMARY OF THE INVENTION

Applicant has unexpectedly produced an encapsulated product, comprising:
  a) a therapeutically-effective amount of a pharmaceutical;
  b) at least one compressible material;
  c) at least one lubricating material; and
  d) wherein said product is in the form of a caplet having a diameter from about 1 millimeter to about 7 millimeters and a length from about 1 millimeter to about 7 millimeters.

In a preferred embodiment, the pharmaceutical incorporated into the encapsulated product is selected from the group consisting of: antibiotics, antitussives, antihistamines, decongestants, alkaloids, mineral supplements, laxatives, antacids, ion exchange resins, anti-cholesterolemics, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psychotropics, antimanics, stimulants, gastrointestinal agents, sedatives, anti-diarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypontics, anti-emetics, anti-nausants, anti-convulsants, neuromuscular drugs, hyper— and hypoglycemic spasmodics, uterine relaxants, mineral and nutritional additives, antiobesity drugs, anabolic drugs, erythropoetic drugs, antiashmatics, cough suppressants, mucolytics, anti-uricemic drugs and mixtures thereof.

An advantage of method of the inventive subject matter is that no heat nor moisture is required for forming the encapsulated product. High levels of active ingredients are obtainable in the products of the inventive subject matter, even though heat or moisture is not required for forming the encapsulated product. In addition, the encapsulated product of the present inventive subject matter has a uniform active ingredient content and may be strong enough to withstand mechanical pressure both in the processing of the product, and in the chewing of the product in the mouth so that the active ingredients are released in the stomach.

DETAILED DESCRIPTION OF THE INVENTION

The encapsulated product of the present invention is a caplet containing a surprisingly high amount of an active ingredient. Applicant has unexpectedly determined that pharmaceuticals can be entrapped by adsorption and compressed with high load into a small encapsulated product. The void space of the resultant product is very low, particularly when polyols are used as the compressible material, as will be discussed hereinafter.

In a preferred embodiment of the present invention, the encapsulated product of the present inventive subject matter is a caplet shaped like a capsule and having a diameter from about 1 millimeter to about 7 millimeters and a length from about 1 millimeter to about 7 millimeters. Preferably, the diameter of the encapsulated product is about 3 millimeters and the length is about 3 millimeters. The caplets may be coated with a thin surface film to protect the product from moisture or water absorption, and from heat and rupture during processing and chewing.

The alternative method of preparing an encapsulated product of the present inventive subject matter contemplates converting liquid active ingredients into small dry caplets or capsules. Powder materials are also available for conversion using the novel method of the inventive subject matter. The novel method is a simple compression process for compacting high levels of active ingredients into a small piece size.

As used herein, the term "active ingredient" includes pharmaceuticals and medicaments.

As used herein, the expression "mammal" includes without limitation any mammalian subject, such as mice, rats, guinea pigs, cats, dogs, human beings, cows, horses, sheep or other livestock.

The amount of active material present in the inventive compositions will vary depending on the particular active used, but generally will be present in an amount of about 0.001% to 70% by weight of the composition. Preferably, the active ingredients used in the inventive compositions are prophylactic or therapeutic active ingredients. Prophylactic or therapeutic active materials which can be used in the present invention are varied. A non-limiting list of such materials includes the following: antibiotics, antitussives, antihistamines, decongestants, alkaloids, mineral supplements, laxatives, antacids, ion exchange resins, anti-cholesterolemics, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypontics, anti-emetics, anti-nausants, anti-convulsants, neuromuscular drugs, hyper—and hypoglycemic spasmodics, uterine relax-ants, mineral and nutritional additives, antiobesity drugs, anabolic drugs, erythropoetic drugs, antiashmatics, cough suppressants, mucolytics, anti-uricemic drugs and mixtures thereof.

In some embodiments, the anti-ulcer agent (i.e., the ulcer therapeutic) is selected from the group consisting of Omeprazole, Lansoprazole, Ranitidine HCl, Famotidine, Nizatidine, Teprenone, Cimetidine, Rabeprazole sodium, Sulpiride, and mixtures thereof.

Preferred therapeutic active materials contemplated for use in the present inventive subject matter are analgesics. Examples of analgesics useful in the present inventive subject matter, and which are the preferred therapeutic active ingredients, include, without limitation, aspirin, acetaminophen, ibuprophen and mixtures thereof.

Another preferred active material can be selected from the class of prophylactic, abortive or analgesic drugs used to treat migraines. Migraines are defined as headaches that last 4 to 72 hours wherein the patient experiences moderate to severe cranial throbbing. Migraines are also associated with nausea, vomiting, or sensitivity to light, sound or smell.

For prophylactic treatment of migraines, β-blockers, calcium channel blockers, tricyclic antidepressants, or anticonvulsants can be used. Examples of drugs indicated for prophylactic treatment include amitriptyline, methysergide, popranolol, valproate, and verapamil.

For abortive treatment of migraines serotonin receptor activators such as eletriptan, ergotamine, naratriptan, rizatriptan benzoate, sumatriptan succinate, and zolmitriptan can be used. Ergot alkaloid derivatives such as ergoamine tartrate and dihydroergotamine are also effective. Dopamine antagonist anti-emetics such as dimenhydrinate, metoclopramide and prochlorperazine, while indicated for the treatment of nausea, can also be used even if nausea is not prominent.

For analgesic treatment acetaminophen, aspirin, non-asteroidal anti-inflammatory drugs ("NSAID") and opioids can be used in the present invention.

In general, any class of drug indicated for migraine treatment may be used in the present invention. For example, sumatriptan succinate may be incorporated into the encapsulated products of the present invention to effectively deliver sumatriptan succinate to a patient in need thereof. In particular, sumatriptan succinate can be formulated with the present invention in doses ranging from 25, 50, to 100 mg daily. All the examples are non-limiting and it will be understood that other migraine therapeutics may be used with the present inventive subject matter.

Yet another preferred active material used in the composition of the present inventive matter is a psychotropic. Psychotropics are used to treat depression, schizophrenia, anxiety disorders, attention deficit order, obsessive compulsive disorder, senile dementia and certain sleep disorders.

The classes of drugs used in treating depression include selective serotonin reuptake inhibitors ("SSRI's"), heterocyclic antidepressants, monoamine oxidase inhibitors ("MAOI's"), serotonergic-noradrenergics, 5-$HT_2$ antagonists and catecholaminergics. Examples of SSRI'S include fluoxetine HCl, sertraline HCl, paroxetine HCl, and fluvoxamine. Examples of heterocyclic antidepressants include amitriptyline, nortriptyline, imipramine, desipramine, doxepin, trimipramine, clomipramine, protriptyline, amoxapine, and maprotiline. Examples of MAOI's include phenelzine and tranylcypromine. An example of a serotonergic-noradrenergics includes venlafaxine HCl. Examples of 5-$HT_2$ antagonists include trazadone, nefazodone, and mirtazapine. An example of a catecholaminergics includes bupropion. All examples are non-limiting and it will be understood that psychotropics of the disclosed classes may be used with the present inventive subject matter.

In some embodiments, the psychotropic is an antidepressant, which may be selected from the group consisting of Fluoxetine HCl, Paroxetine HCl, Sertraline HCl, and Venlafaxine HCl, Amitriptyline, Nortriptyline, Imipramine, Desipramine, Doxepin, Trimipramine, Clomipramine, Protriptyline, Amoxapine, Maprotiline, Phenelzine, Tranylcypromine, Fluvoxamine, Venlafaxine, Trazodone, Nefazodone, Mirtazapine, Bupropion, and mixtures thereof.

In general, any class of psychotropic drug indicated for treating depression may be used in the present invention. For example, fluoxetine HCl may be incorporated into the encapsulated products of the present invention to effectively deliver fluoxetine HCl to a patient in need thereof. In particular, fluoxetine HCl can be formulated with the present invention in doses ranging from about 10 to 60 mg daily. One of ordinary skill in the art will be able to determine the proper dosage for the remaining disclosed drugs.

For the treatment of anxiety, benzodiazepines may be used with the present inventive subject matter. Specific examples include alprazolam, chlordiazepoxide, clonazepam, clorazepate, diazepam, lorazepam, and oxazepam. However, any class of psychotropic drug indicated for anxiety treatment may be used in the present invention.

In particular, alprazolam may be incorporated into the encapsulated products of the present invention to effectively deliver alprazolam to a patient in need thereof. In particular, alprazolam can be formulated with the present invention in doses ranging from about 0.25 to 0.50 mg to be taken three times daily. One of ordinary skill in the art will be able to determine the proper dosage for the remaining disclosed drugs.

For the treatment of insomnia, drugs belonging to the categories of benzodiazepines, imidazopyridines, antidepressants and non-prescription hypnotics may be used with the present inventive subject matter. Examples of benzodiazepines useful for the treatment of insomnia include midazolam, triazolam, oxazepam, temazepam, lorazepam, estazolam, nitrazepam, diazepam, quazepam, flurazepam, zopiclone and clorazepate. An example of an imidazopyridine includes zolpidem and zolpidem tartarate. Examples of antidepressants include amityiptyline and doxepin.

In particular, zolpidem may be incorporated into the encapsulated products of the present invention to effectively deliver zolpidem to a patient in need thereof. In particular, zolpidem can be formulated with the present invention in doses ranging from about 5.0 to 30.0 mg daily, the preferred range being from about 5.0 to 10.0 mg daily. One of ordinary skill in the art will be able to determine the proper dosage for the remaining disclosed drugs. Moreover, all the examples are non-limiting and it will be understood that other psychotrpoics may be used with the present inventive subject matter.

Still yet another preferred active material used in the composition of the present inventive matter is a gastrointestinal therapeutic. Gastrointestinal therapeutics are used to treat gastritis, nausea and vomiting, gastroesophegal reflux disease, colitis, Crohn's disease and diarrhea. Classes of drugs include proton pump inhibitors, histamine $H_2$ receptor antagonists, terpene analogs, and NSAID'S.

For the treatment of gastritis, drugs such as omeprazole, lansoprazole, ranitidine HCl, famotidine, nizatidine, teprenone, cimetidine, rabeprazole sodium, and sulpiride can be used in the compositions of the present inventive subject matter.

For the treatment of nausea and vomiting, drugs such as ondansetron HCl, granisetron HCl, dolasetron mesylate, and tropisetron may be used.

In particular, omeprazole may be incorporated into the encapsulated products of the present invention to effectively deliver omeprazole to a patient in need thereof. In particular, omeprazole can be formulated with the present invention in doses ranging from about 10.0 to 60.0 mg daily, the preferred range being from about 15.0 to 25.0 mg daily. One of ordinary skill in the art will be able to determine the proper dosage for the remaining disclosed drugs. Moreover, all the examples are non-limiting and it will be understood that other gastrointestinal therapeutics may be used with the present inventive subject matter.

Another preferred active material used in the compositions of the present invention include cardiovascular therapeutics. Cardiovascular therapeutics treat hypertension, angina, myocardial infarction, congestive heart failure, acute coronary syndrome, edema, ventricular tachycardia, hyperaldosteronism, ventricular arrhythmia, cardiac insufficiency, atrial fibrillation, arterial occlusion, cardiac decompensation, and microcirculation activation.

A related class of cardiovascular therapeutics are cholesterol reducers such as 3-hydroxy-3-methylglutaryl coenzymeA ("HMG-CoA") reductase inhibitors. HMG-CoA inhibitors work by blocking an enzyme used to make cholesterol. Blocking cholesterol thereby treats hypercholesterolemia which is a significant cause of cardiovascular disease.

For the treatment of hypercholesterolemia, drugs such as simvastin, atorvastatin calcium, pravastatin sodium, pravastatin, lovastatin, fluvastatin sodium, cerivastatin sodium can be used in the compositions of the present inventive subject matter.

For the treatment of hypertension, drugs such as nifedipine, amlodipine besylate, losartan potassium, lisinopril, felodipine, benazepril HCl, ramipril, irbesartan, verapamil HCl, bisoprolol fumarate and hydrochlorothiazide, amlodipine and benazepril HCl, clonidine, candesartan, cilexetil, diltiazem, nicardipine, imidapril, trandolapril, eprosartan mesylate, nilvadipine, verapamil HCl, temocapril, prazosin HCl, isradipine, cilazapril, celiprolol, bisoprolol, betazolol HCl, ramipril, nisoldipine, lisinopril, trandolapril, and nisoldipine can be used in the compositions of the present inventive subject matter.

For the treatment of congestive heart failure, drugs such as dioxin, carvedilol, spironolactone, trandolapril, and bisoprolol can be used in the compositions of the present inventive subject matter.

In particular, simvastin may be incorporated into the encapsulated products of the present invention to effectively deliver simvastin to a patient in need thereof. In particular, simvastin can be formulated with the present invention in doses ranging from about 5.0 to 80 mg daily. One of ordinary skill in the art will be able to determine the proper dosage for the remaining disclosed drugs. Moreover, all the examples are non-limiting and it will be understood that drugs from the disclosed classes may also be used with the present inventive subject matter.

Still another preferred active material used in the composition of the present invention is a therapeutic useful for treating allergic rhinitis. The classes of compounds useful for treating allergic rhinitis include alkylamines, ethanolamines, ethylenediamines, piperazines, phenothiazine, piperdines, and nonsedating compounds.

Among the non-sedating compounds that can be used in the present invention are loratadine, fexofenadine HCl, certirizine HCl, and astemizole. Other drugs which can also be used are fluticasone propionate, mometasone furoate, epinastine, beclomethasone dipropionate, triamcinolone acetonide, budesonide, and azelastine.

In particular, loratadine may be incorporated into the encapsulated products of the present invention to effectively deliver loratadine to a patient in need thereof. In particular, loratadine can be formulated with the present invention in doses ranging from about 5.0 to 15 mg daily, with 15 mg daily being the preferred dosage. One of ordinary skill in the art will be able to determine the proper dosage for the remaining disclosed drugs. Moreover, all the examples are non-limiting and it will be understood that other allergic rhinitis therapeutics may be used with the present inventive subject matter.

Still yet another preferred active material used in the composition of the present invention is a therapeutic useful for treating osteoarthritis or rheumatoid arthritis. Rheumatoid arthritis is defined as non-specific, symmetrical inflammation of the peripheral joints, potentially resulting in progressive destruction of articular and periarticular structures. Osteoarthritis is characterized by loss of articular cartilage and hypertrophy of bone. Although osteoarthritis is a degenerative bone disease, symptoms associated with rheumatoid arthritis such as inflammation of the joints occur in a patient diagnosed with osteoarthritis. Accordingly, therapeutics treating rheumatoid arthritis can also be administered to an osteoarthritic patient.

Classes of drugs indicated for osteoarthritis and rheumatoid arthritis include cycloxygenase-2 inhibitors, NSAID'S, biologic response modifiers, pyrimidine synthesis inhibitors and hyaluronic acid. Specific examples of osteoarthritis and rheumatoid arthritis therapeutics include celecoxib, diclofenac sodium, rofecoxib, nabumetone, diclofenac sodium and misoprostol, oxaprozin, meloxicam, piroxicam, etodolac, naproxen, hylan G-F 20, leflunomide, tenoxicam, and naproxen sodium.

In particular, celecoxib may be incorporated into the encapsulated products of the present invention to effectively deliver celecoxib to a patient in need thereof. In particular, celecoxib can be formulated with the present invention in doses ranging from about 150 to 250 mg daily, with 200 mg daily being the preferred dosage. One of ordinary skill in the art will be able to determine the proper dosage for the remaining disclosed drugs. Moreover, all the examples are non-limiting and it will be understood that other osteoarthritis and rheumatoid arthritis therapeutics from the disclosed classes may also be used with the present inventive subject matter.

Another preferred active material used in the composition of the present invention is a therapeutic useful for treating benign prostatic hypertrophy. Benign prostatic hypertrophy is defined as an adenomatous hyperplasia of the periurethral part of the prostrate gland.

Classes of drug useful for the treatment of benign prostatic hypertrophy include alpha blockers, alpha-1 selective adrenoceptor blocking agents and 5-reductase inhibitors. Specific examples of benign prostatic hypertrophy therapeutics include doxazosin mesylate, terazosin HCl, tamsulosin, finasteride, tamsulosin HCl, ethinyl estradiol and levonorgestrel.

In particular, doxazosin mesylate may be incorporated into encapsulated products of the present invention to effectively deliver doxazosin mesylate to a patient in need thereof. In particular, doxazosin mesylate can be formulated with the present invention in doses ranging from about 1 to 16 mg daily. One of ordinary skill in the art will be able to determine the proper dosage for the remaining disclosed drugs. Moreover, all the examples are non-limiting and it will be understood that other benign prostatic hypertrophy therapeutics from the disclosed classes may also be used with the present inventive subject matter.

Yet another preferred active material used in the composition of the present invention is a drug indicated for the treatment of fungal infections. Classes of drugs indicated for the treatment of fungal infections include synthetic triazole, ergosterol inhibitor, and polyene antifungal. Specific examples of drugs indicated for the treatment of fungal infections are itraconazole, ketoconazole, and amphotericin B.

In particular, itraconazole may be incorporated into the encapsulated products of the present invention to effectively deliver itraconazole to a patient in need thereof. In particular, itraconazole can be formulated with the present invention in doses ranging from about 1.0 to 400 mg daily. One of ordinary skill in the art will be able to determine the proper dosage for the remaining disclosed drugs. Moreover, all the examples are non-limiting and it will be understood that other anti-fungals from the disclosed classes may also be used with the present inventive subject matter.

Still yet another preferred active material used in the composition of the present invention is a anti-convulsant. Anti-convulsants are drugs that prevent or relieve convulsions wherein the convulsions are due to epilepsy, seizure disorders, partial seizure disorders or Huntington's disease. Classes of drugs useful for treating these conditions include gamma-aminobutyric analogs, phenyltriazine, antiepileptic agents, benzodiazepines, polysynaptic response inhibitors, sulfamate-substituted monosaccharides, gamma-amino butyric acid uptake inhibitors and benzamides. Specific examples include carbamazepine, topiramate, and tigabine HCl.

In particular, carbamazepine may be incorporated into the encapsulated products of the present invention to effectively deliver carbamazepine to a patient in need thereof. In particular, carbamazepine can be formulated with the present invention in doses ranging from about 100 to 1600 mg daily. One of ordinary skill in the art will be able to determine the proper dosage for the remaining disclosed drugs. Moreover, all the examples are non-limiting and it will be understood that other anti-convulsants from the disclosed classes may also be used with the present inventive subject matter.

Another preferred active material used in the composition of the present invention is an anti-herpetic. Anti-herpetics are used to treat infections from the varicella-zoster virus. Classes of drugs useful for treating herpes include synthetic purine nucleoside analogs, nucleoside analogs, and antiviral agents. Specific examples include acyclovir, valacyclovir HCL and famcyclovir.

In particular, acyclovir may be incorporated into the encapsulated products of the present invention to effectively deliver acyclovir to a patient in need thereof. In particular, acyclovir can be formulated with the present invention in doses ranging from about 200 to 800 mg daily. One of ordinary skill in the art will be able to determine the proper dosage for the remaining disclosed drugs. Moreover, all the examples are non-limiting and it will be understood that other anti-herpetics from the disclosed classes may also be used with the present inventive subject matter.

Yet another active material used in the compositions of the present invention are anti-diarrheal therapeutics. Anti-diarrheal therapeutics treat the condition of diarrhea whether it is symptomatic of the disorder itself wherein diarrhea is a condition that occurs when a mammal has a low amount of stool in a bowel movement. Diarrhea results mainly from excess fecal water in the bowel of the mammal. Specific examples of anti-diarrheal therapeutics include loperamide HCl, diphenoxylate, codeine phosphate, camphorated opium tincture.

The encapsulated product of the present inventive subject matter contemplates the inclusion of flavors with the pharmaceuticals and medicaments. The flavoring agents which may be used include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Nonlimiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including, without limitation, lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, artificial vanilla, cinnamon derivatives, and various fruit flavors, whether employed individually or in admixture.

Other useful flavorings include aldehydes and esters such as cinnamyl acetate, cinnamaldehyde, citral diethylacetal, dihydrocarvyl acetate, eugenyl formate, p-methylamisol, and so forth may be used.

When flavors are incorporated into the encapsulated products of the present inventive subject matter, the encapsulated product is made according to the following method. If the flavor to be added is liquid, then the liquid flavor is first absorbed onto a solid absorbent. Examples of absorbents on which the liquid may be absorbed include, without limitation, silica gel particles, starches, carbohydrates such as sugars and polyhydroxyalcohols, celluloses, calcium salts such as calcium phosphate, calcium carbonate, and calcium sulfonate, and other absorbing agents in free-flowing powder form. The amount of liquid flavor added depends on the final concentration desired. Generally, though, the liquid flavor will be present in quantities from about 0.1% to 70% by weight of the resultant flavor/absorbent mixture.

The flavor/absorbent mixture is then mixed with a compressible material. Selection of a proper compressible material is dependent on whether the final encapsulated product is to be sugar-free or not. If the encapsulated product is to contain sugar, then the compressible material is, without limitation, a sugar product such "Di-Pac" from the Domino Sugar Corp., a dextrose such as "Cantab" from Compton Knowles Inc., or other compressible sugar materials. If, on the other hand, the encapsulated product is to be sugar-free, then examples of the compressible material are, without limitation, sorbitol, isomalt, maltitol, xylitol, lactitol, calcium phosphates, microcrystalline celluloses, polydextrose, erythritols, other compressible materials and mixtures thereof. Preferably, the compressible material is sorbitol. The amount of compressible material to be added will vary depending on the final encapsulated product.

The flavor/absorbent/compressible material mixture is further mixed with a tableting or lubricating material. The lubricating material forms a film around the particles of the material and helps the material flow, compress and eject from the tableting machine. The lubricant or lubricating material may be present in levels up to 5% by weight of the final composition. Examples of usable lubricating materials include, without limitation, fats, emulsifiers, waxes, magnesium stearate, calcium stearate, talc, starches, silicon dioxide, and mixtures thereof. Among the fats, or fatty materials, useful herein include, without limitation, water-insoluble, inert hydrocarbon fats or oils, or their derivatives and mixtures thereof. Such fats or fatty materials include, for example and without limitation, cocoa butter, hydrogenated vegetable tallow, hydrogenated vegetable oils, and derivative mixtures thereof.

Among the emulsifiers useful herein include, without limitation, alkyl aryl sulfonates, alkyl sulfates, sulfonated amides and amines, sulfated and sulfonated esters and ethers, alkyl sulfonates, polyethoxylated esters, mono- and diglycerides, diactyl tartaric esters of monoglyderides, polyglycerol esters, sorbitan esters and ethoxylates, lactylated esters, propylene glycol esters, sucrose esters and mixtures thereof. Among the waxes useful herein include, without limitation, amorphous waxes, anionic emulsifying waxes, bleached waxes, caranda waxes, cetyl esters, cationic emulsifying waxes, microcrystalline waxes, paraffins, refined waxes and mixtures thereof.

The use of particular fats, emulsifiers or waxes may allow the encapsulated product of the present inventive subject matter to provide controlled release of the active ingredient. The controlled release occurs due to the entrapment of the active material in the particular fat, emulsifier or wax.

Furthermore, other additives such as colors, binders, etc. may also be added to this mixture to form the final mixture. The final mixture is then formed into the encapsulated product of the present invention by using a tableting machine. The stations of the tableting machine are set to the desired caplet size, which is from about 1 millimeter to about 7 millimeters diameter and length for the encapsulated.

The use of flavor along with the pharmaceuticals in the encapsulated product allows for flexibility in adding flavor to food items, confectionery products or chewing gum products, while delivering the pharmaceutical active ingredient to the patient. For example, delivery of two or more flavors to a single food item is possible by using encapsulated products containing different flavors in the food item. The delivery of two or more flavors is also possible in confectionery products and chewing gum products.

While the above final step of the method is preferred, other alternate final steps of preparing encapsulated products are contemplated as being within the scope of the inventive subject matter. In particular, the inventive subject matter also contemplates forming larger tablets with the tableting machine, then grinding the larger tablets into smaller pieces. A further final step is forming the sheets of the final product using roller compaction techniques, then grinding the sheets.

Advantages of preparing the inventive encapsulated product in this manner are that no heat and no moisture are needed in this process. Additionally and surprisingly, high concentrations of flavor (as well as other active ingredients) may be incorporated into the final encapsulated product. Furthermore, the encapsulated product of the present inventive subject matter is small enough that when the confectionery or chewing gum product is chewed, the encapsulated product can pass with the saliva and not be disformed by the teeth of the individual chewing, thus allowing the pharmaceutical or medicament to pass to the gastrointestinal tract.

The present inventive subject matter also contemplates incorporating sweeteners into the encapsulated products. Examples of sweeteners that are available to be mixed in the encapsulated products of the present inventive subject matter include, without limitation, solid natural or synthetic sweeteners such as amino acid based sweeteners, dipeptide sweeteners, especially aspartame, glycerrhizin, saccharin and its salts, acesulfame salts, cyclamates, steviosides, talin, dihydrochalcone compounds and mixtures thereof. The sweetener is generally present in the encapsulated product from about 0.1% to about 70% by weight of the final encapsulated product. The present inventive subject matter also contemplates having a blend of the above sweeteners as the active ingredient in the encapsulated product.

The present inventive subject matter also contemplates the use of the encapsulated product in a food item, a confectionery product or a chewing gum product.

As used herein, the term "confectionery" means a product containing a bulking agent selected from a wide variety of materials such as sugar and, in the case of sugarless bulking agents, sugar alcohols such as sorbitol and mannitol. Confectionery material may include exemplary substances as lozenges, tables, toffee, nougat, chewy candy and so forth, In general, the bulking agent will comprise from about 5 to about 99% and preferably 20 to 95% by weight of the activated confectionery product.

Lozenges are forms intended to be sucked and held in the mouth. They may be in the form of various shapes, the most common being flat, circular, octagonal and biconvex forms. The lozenge bases are generally in two forms, hard boiled candy lozenges and compressed tablet lozenges.

The hard boiled candy lozenges are prepared from a mixture of sugar and other carbohydrates that are kept in an amorphous or glassy condition. This form can be considered a solid syrup of sugars generally having form about 0.5 to about 1.5% moisture. Such materials normally contain up to about 92% corn syrup, up to about 70% sugar and form 0.1% to about 5.0% water. The syrup component generally is prepared from corn syrups high in dextrose, by may include other materials. Further active ingredients such as flavoring, sweeteners, vitamins, minerals, and the like may also be added in accordance with the present invention.

Boiled candy lozenges may also be prepared from nonfermentable sugars such as sortitol, mannitol, and hydrogenated corn syrup. A typical hydrogenated corn syrup ois lycasin. The candy lozenges may contain up to about 95% sorbitol, a mixture of sorbitol and mannitol at a ration of about 9.5 to 0.5 up to about 7.5 to 2.5 and hydrogenated corn syrup up to about 55% of the syrup component.

Soft confectionery items include nougat, chewy candy and the like. These materials contain two primary components, namely a high boiling syrup such as corn syrup or the like, and a relatively light texture frappe, generally prepared form gelatin, egg albumen, milk proteins such as casein, and vegetable proteins such as soy protein, and the like. The frappe is generally relatively light, and may, for example, range in density from about 0.5 to about 0.7 g/cc.

The procedure to make soft confectionery items generally involves the formation of a boiled sugar-corn syrup blend to which is added a frappe mixture. The boiled sugar-corn syrup blend may be prepared from sugar and corn syrup blended in parts by weighy ratio of about 90 to 10 to about 10 to 90. This blend is heated to temperatures above 121° C. to remove water and to form a molten mass. The frappe is generally prepared from gelatin, egg albumen, milk proteins such as casein, and vegetable proteins such as soy protein, and the like which are added to a gelatin solution and rapidly mixed at ambient temperature to form an aerated sponge-like mass. The frappe is then added to the molten candy base and mixed until homogenous at temperatures between 65° C. and 121° C.

The encapsulated product of the present invention can then be added as the temperature of the mixture is lowered to about 65-93° C., whereupon additional ingredients may be further added. The soft confectionery formulation is then cooled and formed to pieces of desired dimensions.

As is stated above, the inventive subject matter also includes the incorporation of the encapsulated product into a chewing gum product. As used herein, the term chewing gum means a product containing a chewing gum formulation. In general, the chewing gum formulation will comprise from about 5 to about 99% and preferably 20 to about 95% by weight of the enhanced chewing gum product.

With regard to a chewing gum formulation, such formulations will contain a gum base and various additives, such as sweeteners and flavors which may be supplied by the encapsulated product of the present invention. The gum base employed will vary greatly depending on various factors such as the type of base used, consistency desired and other components to make the final product. In general, amounts of about 5% to about 45% by weight of the final chewing gum composition are acceptable for use in chewing gum compositions with preferred amounts of about 15% to about 25% by weight. The gum base may be any water-soluble gum base well known in the art. Illustrative examples of suitable polymers in gum bases include both natural and synthetic elastomers and rubbers. For example, those polymers which are suitable in gum bases, include, without limitation, substances of vegetable origin such as chicle, jelutong, gutta percha and crown gum. Synthetic elastomers such as butadiene-styrene copolymers, isobutylene-isoprene copolymers, polyethylene, polyisobutyliene and polyvinylacetate and mixtures thereof, are particularly useful.

The gum base component may contain elastomer solvents to aid in softening the elastomer component. Such elastomer solvents may comprise methyl, glycerol and pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, pentaerythritol ester of wood rosin, glycerol ester of polymerized rosin, glycerol ester of tall oil rosin, glycerol ester of wood rosin and partially dydrogenated wood rosin and partially hydrogenated methyl ester of rosin, such as polymers of alpha-pinene and beta-pinene; terpene resins including polyterpene and mixtures thereof. The solvent may be employed in an amount ranging from about 10% to about 75% and preferably about 45% to about 70% by weight to the gum base.

A variety of traditional ingredients such as plasticizers or softeners such as lanolin, stearic acid, sodium stearate, potassium stearate, glyceryl triacetate, glycerine and the like as well as natural and synthetic waxes, petroleum waxes, such as 35 polyurethane waxes, paraffin waxes and microcrystalline waxes may also be incorporated into the gum base to obtain a variety of desirable textures and consistency properties. These individual additional materials are generally employed in amounts of up to about 30% by weight and preferably in amounts from about 3% to about 20% by weight of the final gum composition.

The chewing gum composition may also include additional fillers such as aluminum hydroxide, alumina, aluminum silicates, calcium carbonate, and talc and combinations thereof. These fillers may also be used in the gum base in various amounts. Preferably the amount of fillers when used will vary from about 4% to about 30% by weight of the final chewing gum composition.

Further, the chewing gum composition will include one or more encapsulated products of the present invention. The encapsulated products of the present invention may provide sweeteners, colorants, and/or flavors to the chewing gum product. The amount of each encapsulated product employed in the chewing gum product will depend on what the encapsulated product is adding to the chewing gum product.

The present inventive subject matter also contemplates the use of the encapsulated product in various other food items, including, without limitation, yogurt, frostings on cakes, nutrition bars, granola bars, candy bars, and the like. The present inventive subject matter also contemplates the use of the encapsulated product in various pharmaceutical applications.

As is stated above, an advantage of method of the inventive subject matter is that no heat nor moisture is required for forming the encapsulated product. In addition, the encapsulated product of the present inventive subject matter has a uniform active ingredient content and may be strong enough to withstand mechanical pressure both in the processing of the product, and in the chewing of the product in the mouth so that the active ingredients are released in the stomach.

The following examples are illustrative of preferred embodiments of the invention and are not to be construed as limiting the invention thereto. All percentages are given in weight percent, unless otherwise noted and equal a total of 100%.

EXAMPLES

Example 1

Preparation of Encapsulated Product Containing Dimenhydrinate

The encapsulated product according to the present inventive subject matter may be made by the following process.

43.5 grams of dimenhydrinate is mixed into 51.3 grams of compressible sucrose to form a mixture. The mixture is then granulated using 3.9 grams of povidone k30, a binder. After mixing with the binder, the material is passed through a no. 10 mesh and allowed to air dry. The dried material is then passed through a no. 20 mesh and mixed with 1.3 grams of magnesium stearate. The final mixture is mixed for 3 minutes. The mixture is loaded into a tableting machine.

A series of caplets 3 millimeters in length and 3 millimeters in diameter is produced using 20 KN of force. The punch is then changed in the tableting machine and a series of caplets 1.3 millimeters in length and 1.3 millimeters in diameter is produced using 20 KN of force.

Example 2

Preparation of Encapsulated Product Containing Nifedipine

The encapsulated product according to the present inventive subject matter may be made by the following process.

34.1 grams of nifedipine is mixed into 51.7 grams of compressible sucrose to form a mixture. The mixture is then granulated using 4.2 grams of plasdone k-29/32, a binder. After mixing with the binder, the material is passed through a no. 10 mesh and allowed to air dry. The dried material is then passed through a no. 20 mesh and mixed with 1.0 grams of magnesium stearate. The final mixture is mixed for 3 minutes. The mixture is loaded into a tableting machine.

A series of caplets 3 millimeters in length and 3 millimeters in diameter is produced using 20 KN of force. The punch is then changed in the tableting machine and a series of caplets 1.3 millimeters in length and 1.3 millimeters in diameter is produced using 20 KN of force.

Example 3

Preparation of Encapsulated Product Containing Nifedipine

The encapsulated product according to the present inventive subject matter may be made by the following process.

34.1 grams of nifedipine is mixed into 60.0 grams of compressible sucrose to form a mixture. The mixture is then granulated using 5.0 grams of plasdone k-29/32, a binder. After mixing with the binder, the material is passed through a no. 10 mesh and allowed to air dry. The dried material is then passed through a no. 20 mesh and mixed with 1.0 grams of magnesium stearate. The final mixture is mixed for 3 minutes. The mixture is loaded into a tableting machine.

A series of caplets 3 millimeters in length and 3 millimeters in diameter is produced using 20 KN of force. The punch is then changed in the tableting machine and a series of caplets 1.3 millimeters in length and 1.3 millimeters in diameter is produced using 20 KN of force.

Example 4

Preparation of Encapsulated Product Containing Nifedipine

The encapsulated product according to the present inventive subject matter may be made by the following process.

34.1 grams of nifedipine is mixed into 59.9 grams of compressible sucrose to form a mixture. The mixture is then granulated using 5.0 grams of plasdone k-29/32, a binder. After mixing with the binder, the material is passed through a no. 10 mesh and allowed to air dry. The dried material is then passed through a no. 20 mesh and mixed with 1.0 grams of magnesium stearate. The final mixture is mixed for 3 minutes. The mixture is loaded into a tableting machine.

A series of caplets 3 millimeters in length and 3 millimeters in diameter is produced using 20 KN of force. The punch is then changed in the tableting machine and a series of caplets 1.3 millimeters in length and 1.3 millimeters in diameter is produced using 20 KN of force.

The inventive subject matter being thus described, it will be obvious that the same may be varied in many ways. Such variations are not to be regarded as a departure from the spirit and scope of the inventive subject matter, and all such modifications are intended to be included within the scope of the following claims.

The invention claimed is:

1. A pharmaceutical product in a compressed caplet form having a diameter and length of from about 1 mm to about 7 mm each, consisting of:
    a) a therapeutically-effective amount of a uniformly distributed pharmaceutical selected from the group consisting of: antibiotics, antiinfectives, cardiovascular therapeutics, gastrointestinal agents, psychotropics and mixtures thereof;
    b) at least one compressible material which is sucrose;
    c) at least one lubricating material in an amount of up to about 5% by weight of the product; and
    d) at least one binder which is polyvinylpyrrolidone k30 or polyvinylpyrrolidone k29/32.

2. The pharmaceutical product of claim 1, wherein the lubricating material is selected from the group consisting of a fat, an emulsifier, a wax, talc, silicon dioxide, and mixtures thereof.

3. The pharmaceutical product of claim 1, wherein the lubricating material is magnesium stearate.

4. The pharmaceutical product of claim 1, wherein the pharmaceutical is present in an amount of about 0.001% to 70% by weight of the product.

5. The pharmaceutical product of claim 1, wherein the caplet has a diameter of about 3 millimeters and a length of about 3 millimeters.

6. The pharmaceutical product of claim 1, wherein the pharmaceutical is a psychotropic.

7. The pharmaceutical product of claim 6, wherein said psychotropic is an anti-anxiety therapeutic.

8. The pharmaceutical product of claim 6, wherein the psychotropic is an insomnia therapeutic.

9. The pharmaceutical product of claim 6, wherein the psychotropic is an antidepressant.

10. The pharmaceutical product of claim 9, wherein the antidepressant is selected from the group consisting of Fluoxetine HCl, Paroxetine HCl, Sertraline HCl, and Venlafaxine HCl, Amitriptyline, Nortriptyline, Imipramine, Desipramine, Doxepin, Trimipramine, Clomipramine, Protriptyline, Amoxapine, Maprotiline, Phenelzine, Tranylcypromine, Fluvoxamine, Venlafaxine, Trazodone, Nefazodone, Mirtazapine, Bupropion, and mixtures thereof.

11. The pharmaceutical product of claim 10, wherein the pharmaceutical is Fluoxetine HCl.

12. The pharmaceutical product of claim 10, wherein the pharmaceutical is Venlafaxine HCl.

13. The pharmaceutical product of claim 1, wherein the pharmaceutical is a gastrointestinal agent.

14. The pharmaceutical product of claim 13, wherein the gastrointestinal agent is an ulcer therapeutic.

15. The pharmaceutical product of claim 14, wherein the ulcer therapeutic is selected from the group consisting of Omeprazole, Lansoprazole, Ranitidine HCl, Famotidine, Nizatidine, Teprenone, Cimetidine, Rabeprazole sodium, Sulpiride, and mixtures thereof.

16. The pharmaceutical product of claim 15, wherein the ulcer therapeutic is Omeprazole.

17. The pharmaceutical product of claim 1, wherein the pharmaceutical is a cardiovascular therapeutic.

18. The pharmaceutical product of claim 17, wherein the pharmaceutical is selected from the group consistinf of nifedipine, amlodipine besylate, losartan potassium, lisinopril, felodipine, benazepril HCl, ramipril, irbesartan, verapamil HCl, bisoprolol fumarate and hydrochlorothiazide, amlodipine and benazepril HCl, clonidine, candesartan, cilexetil, diltiazem, nicardipine, imidapril, trandolapril, eprosartan mesylate, nilvadipine, verapamil HCl, temocapril, prazosin HCl, isradipine, cilazapril, celiprolol, bisoprolol, betazolol HCl, ramipril, nisoldipine, lisinopril, trandolapril, and nisoldipine.

* * * * *